US010092587B2

(12) United States Patent
Kwon et al.

(10) Patent No.: US 10,092,587 B2
(45) Date of Patent: Oct. 9, 2018

(54) ANTIVIRAL COMPOSITION CONTAINING MATERIAL INVOLVED IN PHOSPHATIDYLCHOLINE SYNTHESIS PATHWAY

(71) Applicant: Korea Research Institute of Bioscience and Biotechnology, Daejeon (KR)

(72) Inventors: Dur Han Kwon, Daejeon (KR); Mi Jin Jang, Daejeon (KR); Jae Hyoung Song, Chuncheon-si (KR); Gansukh Enkhtaivan, Daejeon (KR); Sei Ryang Oh, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 0 days.

(21) Appl. No.: 15/389,248

(22) Filed: Dec. 22, 2016

(65) Prior Publication Data
US 2017/0173065 A1 Jun. 22, 2017

Related U.S. Application Data

(63) Continuation-in-part of application No. PCT/KR2015/006469, filed on Jun. 25, 2015.

(30) Foreign Application Priority Data

Jun. 25, 2014 (KR) ........................ 10-2014-0078364

(51) Int. Cl.
*A01N 43/04* (2006.01)
*A61K 31/70* (2006.01)
*A61K 31/7056* (2006.01)
*A61K 31/685* (2006.01)
*A61K 9/14* (2006.01)
*A61K 9/20* (2006.01)
*A61K 9/48* (2006.01)
*A61K 9/00* (2006.01)
*A23L 33/15* (2016.01)
*A23L 33/135* (2016.01)
*A23L 33/10* (2016.01)
*A61K 31/706* (2006.01)
*A61K 31/7064* (2006.01)
*A61K 31/7068* (2006.01)

(52) U.S. Cl.
CPC .......... *A61K 31/7056* (2013.01); *A23L 33/10* (2016.08); *A23L 33/135* (2016.08); *A23L 33/15* (2016.08); *A61K 9/0056* (2013.01); *A61K 9/14* (2013.01); *A61K 9/20* (2013.01); *A61K 9/48* (2013.01); *A61K 31/685* (2013.01); *A23V 2002/00* (2013.01); *A61K 31/706* (2013.01); *A61K 31/7064* (2013.01); *A61K 31/7068* (2013.01)

(58) Field of Classification Search
None
See application file for complete search history.

(56) References Cited

U.S. PATENT DOCUMENTS 4,046,879 A * 9/1977 Swetly .................. A61K 31/70
424/603

FOREIGN PATENT DOCUMENTS

| JP | 01-029319 | 1/1989 |
| JP | 2012-056896 A | 3/2012 |
| JP | 2013-166699 | 8/2013 |
| KR | 10-1995-0702122 A | 6/1995 |
| KR | 100131077 B1 | 11/1997 |
| KR | 10-2000-0064374 A | 11/2000 |
| KR | 10-2012-0002981 A | 1/2012 |

OTHER PUBLICATIONS

Shi et al. Arch. Virol. (2007), vol. 152, pp. 1447-1455.*
Song et al. Journal of Ginseng Research (2014), vol. 38, pp. 173-179.*
R.B. Turner, et al. "Efficacy of Tremacamra, a Soluble Intercellular Adhesion Molecule 1, for Experimental Rhinovirus Infection a Randomized Clinical Trial", Journal of American Medical Association, 1999; 281: 1797-1804.
Q.M. Wang, "Protease inhibitors as potential anti-viral agents for the treatment of picornaviral infections", Progress in Drug Research, vol. 52 (E. jucker, Ed.); 1999 Birkhauser Verlag, Basel; Switzerland.
Shu-Hui Chen, et al., "Synthesis and Evaluation of Tripeptidyl α-Ketoamides as Human Rhinovirus 3C Protease Inhibitors", Bioorganic & Medicinal Chemistry Letters 13 (2003) 3531-3536.
P.S. Dragovich, et al., "Structure-Based Design, Synthesis, and Biological Evaluation of Irreversible Human Rhinovirus 3C Protease Inhibitors. 6. Structure-Activity Studies of Orally Bioavailable, 2-Pyridone-Containing Peptidomimetics", J. Med. Chem. 2002, 45, 1607-1623.
M.J. Otto, et al., "In Vitro Activity of WIN 51711, a New Broad-Spectrum Antipicornavirus Drug" Antimicrobial Agents and Chemotherapy, Jun. 1985, p. 883-886.
R.N. Brown, et al., "2-Ethoxybenzuxazole as a bioisoteric replacement of an ethyl benzoate group in a human rhinovirus (HRV) capsid binder", Bioorganic & Medicinal Chemistry Letters 15 (2005) 2051-2055.

(Continued)

*Primary Examiner* — Patrick T Lewis
(74) *Attorney, Agent, or Firm* — John P. White; Cooper & Dunham LLP

(57) ABSTRACT

The present invention relates to an antiviral composition comprising any one selected from the group consisting of chlorine, phosphocholine, cytidine triphosphate, CDP-choline, phosphorylcholine, and phosphatidylcholine. The antiviral composition is harmless to the human body and exhibits an excellent inhibitory effect on virus proliferation. Therefore, it can be applied to a pharmaceutical composition for preventing or treating viral diseases as well as a health functional food, a quasi-drug composition, and a feed composition for preventing or ameliorating viral diseases.

10 Claims, 5 Drawing Sheets

(56) References Cited

OTHER PUBLICATIONS

D.C. Pevear, et al., "Activity of Pleconaril against Enteroviruses", Antimicrobial Agents and Chemotherapy, Sep. 1999, p. 2109-2115.
Luis Carroasco, "Picornavirus Inhibitors", Pharmac. Ther. vol. 64, pp. 215-290, 1994, Elsevier Science Ltd., Printed in Great Britain.
G.D. Hsiung and Jen-Ren Wang, "Enterovirus infections with special reference to enterovirus 71", J Microbiol Immunol Infect 2000;33:1-8.
K.M. Phipps, et al., "Small interfering RNA molecules as potential anti-human rhinovirus agents: in vitro potency, specificity, and mechanism", Antiviral Research 61 (2004) 49-55.
Arias, et al., "Determinants of RNA-Dependent RNA Polymerase (in)fidelity Revealed by Kinetic Analysis of the Polymerase Encoded by a Foot-and-Mouth Disease Virus Mutant with Reduced Sensitivity to Robavirin", Journal of Virology, Dec. 2008, p. 12346-12355.
L. Fengqin, et al., "The heart-protective mechanism of Qishaowuwei formula on murine viral myocarditis induced by CVB3", Journal of Ethnopharmacology 127 (2010) 221-228.
H.J. Choi, et al., "Anti-Human Rhinovirus Activity of Raoulic Acid from *Raoulia austr'alis*", Journal of Medicinal Food, J Med Food 13 (2) 2010, 326-328.
Mamta K. Jain and Cindy Zoellner, "Role of ribavirin in HCV treatment response: now and in the future", Expert Opin. Pharmacother. (2010) 11 (4) : 673-683.
R. Mac Nicholas and S. Norris, "Review article: optimizing SVR and management of the haematological side effects of peginterferon/ribavirin antiviral therapy for HCV—the role of epoetin, G-CSF and novel agents", Aliment Pharmacol Ther 31, (2010) 929-937.
A.L. Henneberry, et al., "Phosphatidylcholine Synthesis Influences the Diacylglycerol Homeostasis Required for Sec14p-dependent Golgi Function and Cell Growth", Molecular Biology of the Cell vol. 12, 511-520, Mar. 2001.
E.J. Buenz and C.L. Howe, "Picornaviruses and cell death", Trends in Microbiology vol. 14 No. 1 Jan. 2006.
International Search Report in connection with PCT International Application No. PCT/KR2015/006469.

\* cited by examiner

ANTIVIRAL COMPOSITION CONTAINING MATERIAL INVOLVED IN PHOSPHATIDYLCHOLINE SYNTHESIS PATHWAY

CROSS-REFERENCE TO RELATED APPLICATIONS

This application is a continuation-in-part of PCT International Application No. PCT/KR2015/006469, filed Jun. 25, 2015, claiming priority of Korean Patent Application No. KR 10-2014-0078364, filed Jun. 25, 2014, the contents of each of which are hereby incorporated by reference into the application.

TECHNICAL FIELD

The present invention relates to a composition for inhibiting viral proliferation, comprising at least one substance involved in phosphatidylcholine synthesis pathway, a pharmaceutical composition for preventing or treating viral diseases comprising the same, and a health functional food composition, a quasi-drug composition, and a feed composition for preventing or ameliorating viral diseases.

BACKGROUND ART

*Picornavirus* is a positive single-stranded RNA virus with 7.2 Kb to 8.5 Kb, in which an RNA genome is only 7500 nt long. In addition, the virus is a very small globular non-enveloped virus with a size of approximately 22 nm to 30 nm, and is the oldest known virus. *Rhinovirus, enterovirus, cardiovirus, aphthovirus, hepatovirus*, etc. belong to *picornavirus*.

At least 50% of cold-inducing pathogenic viruses are *rhinovirus*. However, therapeutic agents against *rhinovirus* infection have not yet been developed. As drugs that inhibit *rhinoviruses*, tremacamra (Turner R B et al., 1999, JAMA 281:1797-1804) which is a drug inhibiting *rhinoviruses* to be bound to ICAM-1, a receptor, in the form of sICAM-1, and a drug (Wang, Q M, 2001. Prog. drug Res. 229-253; Chen D H et al., 2003. Bioorg Med Chem Lett 13:3531-3536.; Dragovich P S et al., 2002. J Med Chem 45:1607-1623) which has a function to inhibit *rhinovirus* (HRV) 3C protease have been reported.

However, the tremacamra, a spray-type formulation, is disadvantageous in that it requires numerous administrations per day and that an effect thereof is low. Although an HRV 3C protease inhibitor was proved effective against HRV 14 in an in vitro experiment (Chen S H et al., 2003. Bioorg Med Chem Lett 13:3531-3536), a significant result was not obtained in an experiment using a monkey as an infectious model (Dragovich P S et al., 2002. J Med Chem 45:1607-1623).

Additionally, as formulations that react with a virus capsid, WIN 51711 (Otto M J et al., 1985, Antimicrob Agents Chemother 27(6):883-886), pirodavir (Brown R N et al., 2005. Bioorg Med Chem Lett 15(8): 2051-2055), and pleconaril (Pevear D C et al., 1999. Antimicrob Agents Chemother 43(9):2109-2115) have been reported. Further, enviroxime (Carraso L., 1994. 64:215-290) is being developed as a viral RNA synthesis inhibitor.

However, the pirodavir has a property that pharmacokinetic values are low even if it inhibits the proliferation of various *rhinovirus* serotypes. Further, the pirodavir also has a property to be easily hydrolyzed, and thus cannot be progressed to be used as a therapeutic agent. The pleconaril has a wide range of applications, such as *rhinovirus, enterovirus*, etc. (Hsiung G D & Wang J R 2000. J Microbiol Immunol Infect 33(1):1-8), but has not yet been approved by the US Food and Drug Administration (USFDA) due to drug interaction, marginal efficacy, and production of virus resistance.

Recently, RNAi has also been investigated as a therapeutic drug (Phipps et al., 2004. Antiviral Res. 61:49-55). However, it is disadvantageous in that target RNAi needs to be prepared separately depending on more than 100 types of *rhinoviruses*

On the other hand, ribavirin is a compound in the form in which triazole carboxamide is bound to a ribose sugar. Further, the ribavirin has been reported to exhibit antiviral ability against FMD virus causing foot-and-mouth disease (Arias A et al., 2008, J Virol 82(4): 12346-12355), *enterovirus* causing hand-foot-mouth disease (Fengqin L et al., 2010 J Ethnopharmacol 127(2):221-228), and *rhinovirus* (Choi H J et al., 2010 J med Food 13(2): 326-328), which belong to the family Picornaviridae. Furthermore, the ribavirin is a drug used as a therapeutic agent along with interferon for treating infectious diseases of hepatitis C virus, a *hepatovirus* (Jain M K & Zoellner C 2010 Expert Opin Pharmacother 11(4):673-683).

However, the ribavirin is known to exacerbate heart disease by inducing severe anemia and is disadvantageous in that it induces various side effects, such as fatigue, headache, etc. (MacNicholas R & Norris S 2010 Aliment Pharmacol Ther 31(9):929-937). In this regard, there is a growing necessity to develop antiviral agents exhibiting significant antiviral effects without any side effects.

*Enterovirus* infection may cause cold, myocarditis, meningitis, hand-foot-mouth disease, etc., or may cause a neurological disorder. It is known that there are no therapeutic agents against *enterovirus*, except for symptomatic treatment.

DISCLOSURE

Technical Problem

The present inventors have made an extensive effort to develop an antiviral agent showing a significant antiviral effect without side effects. As a result, it was confirmed that substances involved in phosphatidylcholine synthesis pathway from choline to phosphatidylcholine show significant anti-proliferative ability against virus, and has efficacy as a therapeutic agent against viral infection, thereby completing the present invention.

Technical Solution

A main object of the present invention is to provide an antiviral composition comprising at least one substance involved in phosphatidyl synthesis pathway.

Another object of the present invention is to provide a pharmaceutical composition for preventing or treating viral diseases, comprising the composition.

A further object of the present invention is to provide a health functional food, a quasi-drug composition, and a feed composition for preventing or ameliorating viral diseases, comprising the composition.

Advantageous Effects

The composition for inhibiting viral proliferation according to the present invention exhibits an inhibitory effect on virus proliferation, and thus can be applied to a pharmaceutical composition for preventing or treating viral diseases as well as a health functional food, a quasi-drug composition, and a feed composition for preventing or ameliorating viral diseases.

BEST MODE

In one aspect for achieving the above objects, the present invention provides an antiviral composition comprising at least one substance involved in phosphatidylcholine synthesis pathway.

The substance involved in the phosphatidylcholine synthesis pathway refers to choline, phosphocholine, cytidine triphosphate, CDP-choline, phosphorylcholine, or phosphatidylcholine.

Choline is changed to phosphocholine by choline kinase under the influence of adenosine triphosphate (ATP). Meanwhile, cytidine, a type of nucleoside, is changed to cytidine triphosphate (CTP) by phosphorylation. CDP-choline is formed when cytidine triphosphate is added to phosphocholine (A. L.Henneberry and three others, 2001. Mole. Bioliology of the Cell 12:511-520p). Phosphatidylcholine is formed when diacylglycerol is added to CDP-choline.

Figure 1:
FIG. 1 shows a series of schematic illustration in which human *rhinovirus* induces host cell necrosis so that progeny virus is released therefrom to induce a cold.

As shown in FIG. 1, proteases 2A and 2C in a virus activate caspase-3 to induce necrosis of host cells. Progeny viruses produced in host cells firstly infected by necrosis of the host cells are very easily propagated to other cells (Buenz E J & Howe C L. Trends in Microbiology. 2006. 14(1): 28-36). Therefore, viral diseases, such as a cold, etc., are induced.

Figure 2:
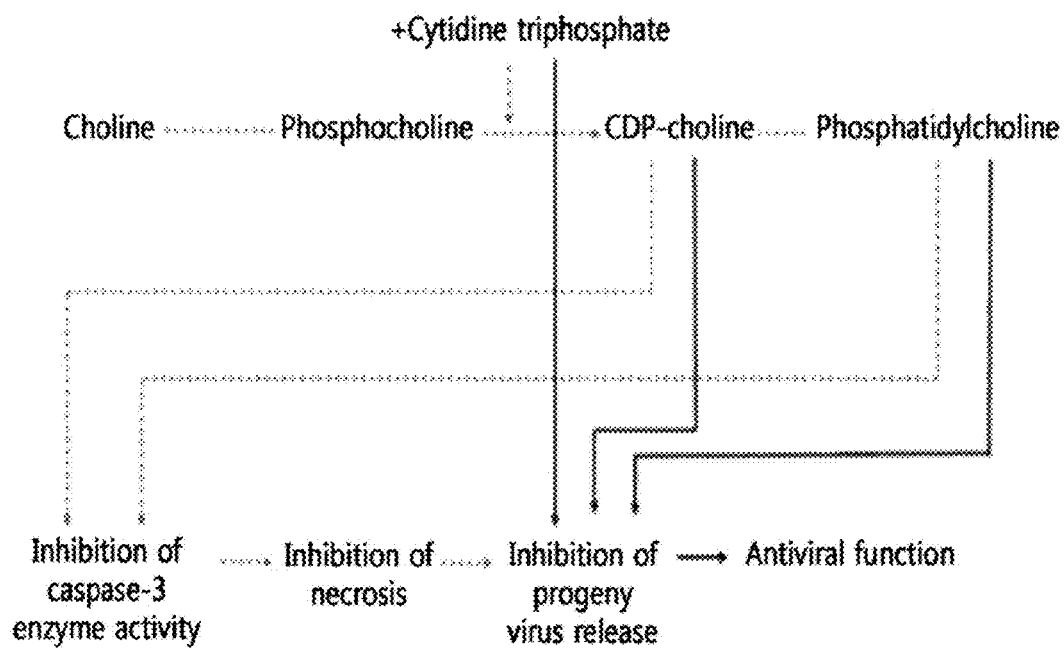
FIG. 2 shows an action mechanism of substances involved in phosphatidylcholine synthesis pathway of the present invention.

The present inventors found that the substance of the present invention involved in the phosphatidylcholine synthesis pathway inhibits the activation of caspase-3 in a virus, inhibits cell necrosis, and suppresses the release of progeny viruses, thereby confirming that the substance exhibits antiviral abilities (FIG. 2).

As used herein, the term "anti-virus" refers to inhibition of virus proliferation.

In one specific embodiment, the virus may refer to *picornavirus*. *Picornavirus* is a positive single-stranded RNA virus with 7.2 Kb to 8.5 Kb, in which an RNA genome is only 7500 nt long. In addition, the virus is a very small globular non-enveloped virus with a size of approximately 22 nm to 30 nm, and is the oldest known virus.

In another specific embodiment, the virus may be *rhinovirus, enterovirus, cardiovirus, aphthovirus*, or *hepatovirus*. The *rhinovirus* may be *rhinovirus* type 2, type 3, or type 5.

The *rhinovirus* is a hospital virus of a common cold (sinus cold), and currently more than 100 serotypes of 1 (A, B), and 2 to 113 are known. In particular, *rhinovirus* is a virus that uses single-stranded RNA as a genome and has RNA polymerase, thereby propagating without DNA stage. It contrasts with HIV which propagates through the process of changing to DNA because HIV has an RNA reverse transcriptase.

The *enterovirus* commonly refers to a virus causing infections in the intestines of humans and mammals and includes poliovirus, coxsackievirus, and echovirus. Inflammation, rash, etc. may occurr in hands, feet, and a mouth to cause hand-foot-mouth disease at the onset of *enterovirus*. However, aseptic meningitis, viral pneumonia, encephalitis, acute flaccid paralysis is accompanied for some patients. For infants whose immune system has not yet developed, they may die from pulmonary edema in some severe cases. In particular, poliovirus refers to a virus causing infantile paralysis, and coxsacki A virus and *enterovirus* 71(EV71) cause hand-foot-mouth disease in humans, wherein the symptoms thereof are similar to that of foot-and-mouth disease. Coxsackievirus type B causes pancreatitis.

The *cardiovirus* may comprise encephalomyocarditis virus.

The *aphthovirus* is a virus that causes foot-and-mouth disease and is very small in size, having a diameter of only 25 nm to 30 nm. The *aphthovirus* is a bipolar single-stranded non-enveloped RNA virus, capable of making proteins by using its own RNA as mRNA.

The *hepatovirus* may comprise hepatitis A virus.

The present inventors treated HeLa cells, which were infected by *rhinovirus* type 2, type 3, or type 5, with the antiviral composition according to the present invention. As a result, it was confirmed that the composition has an antiviral effect that is superior to that of ribavirin, an antiviral agent used as the control group (Example 1). Therefore, the antiviral composition according to the present invention has the effect of inhibiting proliferation of various viruses which activate caspase-3 to induce cell necrosis.

Another aspect of the present invention is to provide a pharmaceutical composition for preventing or treating a viral disease, comprising the antiviral composition of the present invention.

The antiviral composition refers to a composition comprising at least one substance involved in phosphatidylcholine synthesis pathway. The substance involved in the phosphatidylcholine synthesis pathway refers to choline, phosphocholine, cytidine triphosphate, CDP-choline, phosphorylcholine, or phosphatidylcholine. The substance may be commercially available one that is purchased.

The viral disease refers to a disease that may occur when animals including humans are infected with a virus. As an example, it may be a disease that occurs as a result of being infected by *picornavirus*. Additionally, as an example, it may be a disease that occurs as a result of being infected by *rhinovirus, enterovirus, cardiovirus, aphthovirus*, or *hepatovirus*.

As one specific embodiment, the viral disease may comprise cold, enteritis, hand-foot-mouth disease, viral meningitis, pneumonia, encephalitis, neurogenic pulmonary edema, conjunctivitis, encephalomyocarditis, myocarditis, hepatitis, poliomyelitis, paralysis, vesicular disease, myositis, pancreatitis, epidemic myalgia, herpangina, asthma, chronic obstructive pulmonary disease, sinusitis, or tympanitis. Specifically, the viral disease may be a cold, enteritis, hand-foot-mouth disease, viral meningitis, pneumonia, encephalitis, acute flaccid paralysis, neurogenic pulmonary edema, acute hemorrhagic conjunctivitis, encephalomyocarditis, myocarditis, and hepatitis A. More specifically, the viral disease may be a cold.

As another specific embodiment, the viral disease may be foot-and-mouth disease. The foot-and-mouth disease is transmitted by direct contact with infected animals' blister fluid, saliva, milk, semen, air during breathing, excreta, etc. In addition, the foot-and-mouth disease is also transmitted by indirect contact, such as work clothes, gloves, shoes, vehicles and feeds of farmers, farm workers, veterinarians, insemination technicians, feed providers, excreta disposers, drivers of slaughterhouses, etc. Not only these, but also it can be infected via air.

As used herein, the term "prevention" may refer to all actions of suppressing or delaying the onset of viral diseases by administering the composition for preventing or treating viral diseases according to the present invention to subjects.

As used herein, the term "treatment" may refer to all actions of improving or ameliorating symptoms of viral diseases by administering the composition of the present invention to subjects who are suspected of developing the viral diseases.

Additionally, the pharmaceutical composition of the present invention may comprise a pharmaceutically effective amount of choline, phosphocholine, cytidine triphosphate, CDP-choline, phosphorylcholine, or phosphatidylcholine.

As used herein, the term "pharmaceutically effective amount" refers to an amount sufficient to treat diseases at a reasonable benefit/risk ratio that is applicable to any medical treatment. The effective dosage level may be determined depending on a subject's type, severity of the disease, the subject's age and gender, activity of the drug, sensitivity to the drug, administration time, administration route, excretion rate, duration of treatment, drugs used in combination with the composition, and other factors well known in the medical field. The pharmaceutical composition of the present invention may be administered alone or in combination with other therapeutic agents, and may be administered sequentially or simultaneously with conventional therapeutic agents. The composition may be administered in a single or multiple dosage form. It is important to administer the composition in the minimum amount that can exhibit the maximum effect without causing side effects, and in view of all the above-described factors, this amount can be easily determined by one of ordinary skill in the art.

The pharmaceutical composition of the present invention may be used by adding a pharmaceutically acceptable salt to at least one substance involved in the phosphatidylcholine synthesis pathway, as an active ingredient. In addition, as the salt, an acid addition salt that is produced by a pharmaceutically acceptable free acid is useful. The active ingredient of the composition may form a pharmaceutically acceptable acid addition salt according to conventional methods in the art. Organic acid and inorganic acid may be used as the free acid. Herein, the inorganic acid may include hydrochloric acid, bromic acid, sulfuric acid, phosphoric acid, etc, and the organic acid may include citric acid, acetic acid, lactic acid, tartaric acid, maleic acid, fumaric acid (facid), formic acid, propionic acid, oxalic acid, trifluoroacetic acid, benzoic acid, gluconic acid, methanesulfonic acid, glycolic acid, succinic acid, 4-toluenesulfonic acid, galacturonic acid, embonic acid, glutamic acid, or aspartic acid, but are not limited thereto.

The pharmaceutical composition of the present invention may be used as a single formulation or prepared as a complex formulation by additionally including a drug known to have an approved antiviral effect. In addition, the pharmaceutical composition of the present invention may be prepared in a unit dosage form by formulating the same using a pharmaceutically acceptable carrier or excipient, or prepared by encapsulating the same in a multiple dose container.

As used herein, the term "pharmaceutically acceptable carrier" may refer to a carrier or a diluent that does not inhibit biological activities and properties of a compound to be administered without irritating an organism. A type of the carrier which can be used in the present invention is not particularly limited, and any carrier can be used as long as it is a pharmaceutically acceptable carrier commonly used in the art. A non-limiting example of the carrier includes saline, sterile water, ringer's solution, buffered saline, albumin injection solution, dextrose solution, maltodextrin solution, glycerol, ethanol, etc. These can be used alone or in combination of two or more.

Additionally, pharmaceutically acceptable additives may be further included, if necessary. Herein, examples of the pharmaceutically acceptable additives include starch, gelatinized starch, microcrystalline cellulose, milk sugar, povidone, colloidal silicon dioxide, calcium hydrogen phosphate, lactose, mannitol, malt, gum arabic, pre-gelatinized starch, corn starch, powdered cellulose, hydroxypropyl cellulose, opadry, sodium glycolate starch, carnauba wax, synthetic aluminum silicate, stearic acid, magnesium stearate, aluminum stearate, calcium stearate, sucrose, dextrose, sorbitol, talc, etc. The pharmaceutically acceptable additive according to the present invention is preferably contained in an amount of 0.1 to 90 parts by weight based on the composition, but is not limited thereto. In addition, other conventional additives such as antioxidants, buffers, and/or bacteristats may be used.

Additionally, the pharmaceutical composition of the present invention may be administered orally and parenterally and be used in various formulations at the time of actual clinical administration. That is, the pharmaceutical composition of the present invention may be prepared by mixing with generally used diluents or excipients, such as fillers, extenders, binders, wetting agents, disintegrating agents, dispersants, lubricants, surfactants, etc. As a result, it may be formulated into injectable formulations such as aqueous solution, suspension and emulsion, pills, capsules, granules, or tablets.

Solid formulations for oral administration include tablets, pills, powders, granules, capsules, etc. and the solid formulations may be prepared by mixing with an excipient, such as starch, calcium carbonate, sucrose, lactose, or gelatin. Further, a lubricant such as magnesium stearate and talc may also be used in addition to a simple excipient.

Liquid formulations for oral administration include a suspension, a liquid, an emulsion, a syrup, etc. In addition to water commonly used as a simple diluent and a liquid paraffin, various excipients, for example, wetting agents, sweetening agents, fragrance agents, preservatives, etc., may be included.

Formulations for parenteral administration may include sterilized aqueous solutions, non-aqueous solvents, suspending agents, emulsions, freeze-drying agents, and suppositories. Propylene glycol, polyethylene glycol, vegetable oils such as olive oil, injectable esters such as ethyl oleate may be used as non-aqueous solvents and suspending agents. Suppositories may include witepsol, macrogol, tween 61, cacao butter, laurin butter, glycerinated gelation, etc.

A further aspect of the present invention is to provide a method for preventing or treating a viral disease, comprising a step of administering a composition for preventing or treating a viral disease to a subject in a pharmaceutically effective amount.

As used herein, the term "administration" refers to introduction of the pharmaceutical composition of the present invention into a subject with any appropriate methods. In addition, as long as the administration route of the composition of the present invention can reach a target tissue, the composition may be orally and parenterally administered through various routes.

The administration method of the pharmaceutical composition according to the present invention is not particularly limited, and the method can be a conventional method used in the art. As a non-limiting example of the administration method, a composition may be administered via oral or parenteral administration method. For parenteral administration, topical application, or intra-abdominal injection, intra-rectal injection, subcutaneous injection, intravenous injection, intramuscular injection, or intrathoracic injection may be preferable. The pharmaceutical composition according to the present invention can be prepared in various formulations depending on the intended administration method.

An administration dosage of the pharmaceutical composition of the present invention can be determined according to a patient's weight, age, gender, health condition, diet, administration time, administration method, excretion rate, and severity of a disease. For example, the effective amount of the pharmaceutical composition of the present invention can be 0.0001 g/kg to 10 g/kg, and preferably 0.001 g/kg to 1 g/kg. In addition, the composition can be administered 1 to 6 times a day. However, the dosage may be increased or decreased depending on the administration route, severity of a disease, gender, weight, age, etc., and thus does not in any way limit the scope of the present invention. The dosage unit can contain, for example, 1, 2, 3, or 4 individual doses, or ½, ⅓, or ¼ of an individual dose. An individual dose preferably contains the amount of an active drug which is administered in one application and which usually corresponds to a whole, ½, ⅓, or ¼ of a daily dose.

As used herein, the term "subject" may refer to all animals including humans in which a viral disease is developed or likely to be developed. The animal may not only include a human but also include a mammal such as a cow, a horse, a sheep, a pig, a goat, a camel, an antelope, a dog, a cat, etc., but is not limited thereto.

As used herein, the term "pharmaceutically effective amount" refers to an amount sufficient to treat diseases at a reasonable benefit/risk ratio that is applicable to any medical treatment. An appropriate total daily dose of the composition can be determined by a physician within the scope of sound medical judgment. Generally, an amount of 0.001 mg/kg to 1000 mg/kg, preferably 0.05 mg/kg to 200 mg/kg, more preferably 0.1 mg/kg to 100 mg/kg can be administered once a day or can be administered in divided doses several times daily. However, for the purposes of the present invention, it is preferable that the specific therapeutically effective amount of the composition administered to a particular patient can be varied depending on the type and degree of the response to be achieved in the treatment, the specific composition, including whether another agent is included in the composition, the patient's age, body weight, general health status, gender and diet, time and route of administration, the secretion rate of the composition, treatment period, other drugs used together or concurrently in the treatment and a variety of factors well known in the medical field.

The present inventors treated HeLa cells, which were infected with a virus, with a composition containing at least one substance involved in the phosphatidylcholine synthesis pathway. As a result, it was confirmed that the composition has an antiviral effect that is superior to that of ribavirin, an antiviral agent used as the control group. Therefore, it was also confirmed that the pharmaceutical composition containing choline, phosphocholine, cytidine triphosphate, CDP-choline, phosphorylcholine, or phosphatidylcholine can be used for prevention and treatment of various viral diseases (Example 1).

Additionally, Vero cells were infected with two types of *enteroviruses*. Thereafter, the infected Vero cells were treated with a composition containing a substance involved in at least one phosphatidylcholine synthesis pathway. As a result, it was confirmed that the antiviral effect increased in proportion to the concentration thereof. In addition, it was also confirmed that the pharmaceutical composition comprising cytidine triphosphate, CDP-choline, phosphorylcholine, or phosphatidylcholine may be used for prevention and treatment of various viral diseases (Example 2).

A still further aspect of the present invention is to provide a health functional food composition for preventing or ameliorating a viral disease, comprising the antiviral composition.

The antiviral composition is a composition containing at least one substance involved in phosphatidylcholine synthesis pathway. The substance involved in the phosphatidylcholine synthesis pathway is choline, phosphocholine, cytidine triphosphate, CDP-choline, phosphorylcholine, or phosphatidylcholine. The substance may be commercially available one that is purchased.

As used herein, the term "amelioration" may refer to all actions that at least reduce a parameter related to the conditions to be treated, for example, the degree of symptom.

As used herein, the term "health functional food" refers to a food prepared or processed into tablet, capsule, powder, granule, liquid, pill, etc. using raw materials or ingredients with useful functions for the human body. Herein, the term "functional" indicates a useful effect for human health, such as regulation of nutrients for the structure and function of the human body, physiological action, or the like. The health functional food of the present invention may be prepared according to a method commonly employed in the art, and raw materials and ingredients commonly used in the art may be added when preparing the health functional food. Since food is used as raw materials, unlike general drugs, the health functional food lacks side effects which may occur when a drug is taken for a long period of time, and may have excellent portability.

When the composition of the present invention is used by containing the same in a health functional food, the composition may be added either alone or together with other health functional foods or food health functional food ingredients, and may be suitably used according to conventional methods. The amount of mixed active ingredients may properly be determined depending on the purpose of use (prevention, health, or therapeutic treatment). Generally, at the time of preparing food, the composition of the present invention is added in an amount of 1% to 10% by weight, preferably 5% to 10% by weight based on the raw material composition. However, the effective amount of the composition in the food composition for the long term intake for health and hygiene, or health control may be below the above range.

The viral diseases are as described above.

A still further aspect of the present invention is to provide a quasi-drug composition for preventing or ameliorating a viral disease, comprising the antiviral composition.

The antiviral composition refers to a composition containing at least one substance involved in phosphatidylcholine synthesis pathway. The substance involved in the phosphatidylcholine synthesis pathway is choline, phosphocholine, cytidine triphosphate, CDP-choline, phosphorylcholine, or phosphatidylcholine. The substance may be commercially available one that is purchased.

As used herein, the term "quasi-drug" may refer to a product corresponding to any one selected from a textile product, a rubber product, or an analogue thereof used for the purpose of treatment, alleviation, handling, or prevention of human or animal diseases; a product which, not being a tool, a machine, or an analogue thereof, has minimal effects or does not have any effect on humans; and a preparation used for the purpose of disinfection, pest control, or a similar use thereof for the prevention of infectious diseases, which, among the products being used for the purpose of treatment, alleviation, handling, or prevention of human or animal diseases, excludes those which are not a tool, a machine, or an analogue thereof; and which, among the products being used for the purpose of rendering a pharmacological effect on the human or animal structures and functions, excludes those which are not a tool, a machine, or an analogue thereof.

Additionally, the quasi-drug may include external skin applications and personal hygiene products. Examples of the quasi-drug composition may include disinfecting cleaners, shower foams, gargles, wet tissues, detergent soaps, hand washes, or ointments, but are not limited thereto.

When the composition according to the present invention is used as a quasi-drug additive, the composition may be added either alone or together with other quasi-drugs or quasi-drug ingredients, and may be suitably used according to conventional methods. The amount of mixed active ingredients may properly be determined depending on the purpose of use.

The present inventors treated HeLa cells, which were infected by a virus, with a composition containing at least one substance involved in the phosphatidylcholine synthesis pathway. As a result, it was confirmed that the composition has an antiviral effect that is superior to that of ribavirin, an antiviral agent used as the control group. Therefore, the antiviral composition may effectively be used in quasi-drugs for treatment, alleviation, handling, or prevention of viral diseases.

The viral diseases are as described above.

A still further aspect of the present invention is to provide a feed composition for preventing or ameliorating a viral disease, comprising the antiviral composition.

The antiviral composition refers to a composition containing at least one substance involved in phosphatidylcholine synthesis pathway. The substance involved in the phosphatidylcholine synthesis pathway is choline, phosphocholine, cytidine triphosphate, CDP-choline, phosphorylcholine, or phosphatidylcholine. The substance may be commercially available one that is purchased.

The feed composition may include feed additives. The feed additive of the present invention refers to feed supplements approved by Control of Livestock and Fish Feed Act.

As used herein, the term "feed" may refer to any natural or artificial diet, meal, or ingredient of the meal for animals to eat, intake, and digest.

The type of the feed is not particularly limited, and conventional feeds that are used in the art may be used. Non-limiting examples of the feed include plant-based feeds, such as grain, nut, food byproduct, seaweed, fiber, drug byproduct, oil, starch, meal, or grain byproduct, and animal-based feeds such as protein, inorganic substance, fat, mineral, oil, single cell protein, zooplankton, or food. These can be used alone or in combination of two or more.

Additionally, the feed additive may additionally contain carriers which are acceptable for a monogastric animal. In the present invention, the feed additive may be used intactly, or well-known carriers, stabilizers, etc. may be added to the feed additive. In addition, as necessary, various nutrients such as vitamins, amino acids, minerals, etc., antioxidants, antibiotics, antimicrobials, and other additives may be added. The feed additive may have appropriate formulations, such as powders, granules, pellets, suspensions, etc. The feed additive of the present invention may be provided alone or in a mixture with feeds, for a monogastric animal.

As one specific embodiment, the viral disease may include cold, enteritis, hand-foot-mouth disease, viral meningitis, pneumonia, encephalitis, neurogenic pulmonary edema, conjunctivitis, encephalomyocarditis, myocarditis, hepatitis, poliomyelitis, paralysis, vesicular disease, myositis, pancreatitis, epidemic myalgia, herpangina, asthma, chronic obstructive pulmonary disease, sinusitis, or tympanitis.

As another specific embodiment, the viral disease may be foot-and-mouth disease. The foot-and-mouth disease is transmitted by direct contact with infected animal's blister fluid, salvia, milk, semen, air during breathing, excreta, etc. In addition, the foot-and-mouth disease may also be transmitted via indirect contact, such as work clothes, gloves, shoes, vehicles and feeds of farmers, farm workers, veterinarians, insemination technicians, feed providers, excreta disposers, drivers of slaughterhouses, etc. Not only these, but also it may be infected via air.

The feed composition of the present invention has an excellent antiviral efficacy and improves resistance and defense against viral diseases, thereby preventing perish and reduction of productivity caused by viral diseases. Accordingly, the feed composition of the present invention has the effect of preventing human infection.

MODE OF THE INVENTION

Hereinbelow, the present invention will be described in detail with accompanying exemplary embodiments. However, the exemplary embodiments disclosed herein are only for illustrative purposes and should not be construed as limiting the scope of the present invention.

As a control group, ribavirin, which is known to have the effect for inhibiting proliferation of FMD virus causing foot-and-mouth disease, *enterovirus* causing hand-foot-mouth disease, *rhinovirus*, and hepatitis C virus, which is a *hepatovirus*, which belong to the family Picornaviridae, was used. Accordingly, experiments that confirm antiviral activities of the antiviral composition of the present invention were conducted, as follows.

EXAMPLE 1

Antiviral Activity Test Against *Rhinovirus*

HeLa cells ($2\times10^4$ cells) were placed in each well of 96-well plates and cultured for 24 hours. After 24 hours, the culture supernatant of each well was removed, and then *rhinovirus* type 2, type 3, and type 5 solutions titrated with TCID50 were placed in each well. The virus used in the present invention was purchased from the American Type Culture Collection (ATCC). Each virus activity thereof was cultured and stored at $-70°$ C. for use.

Ribavirin, which is a control group, cytidine triphosphate, CDP-choline, phosphatidylcholine, and adenosine triphosphate, which are experimental groups, were treated in each well in amounts of 0.1 µg/ml, 1 µg/ml, 10 µg/ml, and 100 µg/ml, respectively. Each compound was purchased from Sigma Corp.

The anti-proliferative ability against a virus was measured according to the methods described in Korean Patent No. 10-0682069. Specifically, after completion of the viral infection test, a 70% acetone solution (100 µl) was added to each well and then allowed to stand at $4°$ C. for 1 hour. Each well was washed with distilled water for several times and dried at room temperature. Thereafter, 100 µl of 0.4% (w/v) SRB sulforhodamine B (SRB) solution dissolved in 1% (v/v) acetic acid was added and stained for 30 minutes. The SRB staining solution that did not bind to cells was washed with 1% (v/v) acetic acid for several times and then dried again.

100 µl of 10 mM Tris solution (pH 10.5) was added in each well so as to sufficiently dissolve the staining solution bound to the cells. Thereafter, the absorbance was measured at 560 nm.

The cell viabilities (%), after treatment with ribavirin, cytidine triphosphate, CDP-choline, phosphatidylcholine, or adenosine triphosphate were calculated using Equation 1 below.

$$\text{Cell viability (\%)}=A/B\times100 \quad \text{[Equation 1]}$$

wherein,

A refers to a group not treated with a virus; and B refers to a group treated only with ribavirin, cytidine triphosphate, CDP-choline, or phosphatidylcholine. In addition, the following C refers to a group treated only with a virus, and the following D refers to a group treated a virus with ribavirin, cytidine triphosphate, CDP-choline, or phosphatidylcholine.

Even if cells were treated with cytidine triphosphate, CDP-choline, or phosphatidylcholine, the cell viability for the wells of the groups to which drugs were not added at the highest administration concentration (100 µg/mL) was 98.69%, 98.69%, 99.36%, respectively. Therefore, since there is no change in the cell viability, the antiviral composition of the present invention can be administered to animals including humans.

Additionally, antiviral abilities of ribavirin, cytidine triphosphate, CDP-choline, phosphatidylcholine, and adenosine triphosphate, e.g., anti-proliferative abilities (%) against a virus, were calculated using Equation 2 below, and the results thereof are shown in Table 1 below. The statistical results are represented by mean values and standard deviations with respect to the resulting values of experiments performed 3 times under the same conditions.

$$\text{Anti-proliferative ability against a virus (\%)}=(D-C)/(B-C)\times100 \quad \text{[Equation 2]}$$

TABLE 1

| Classification | Drug concentration (100 µg/mL) | | |
|---|---|---|---|
| | Rhinovirus type 2 | Rhinovirus type 3 | Rhinovirus type 5 |
| Cytidine triphosphate | 92.77 ± 6.34 | 84.66 ± 7.63 | 56.93 ± 3.27 |
| CDP-choline | 94.66 ± 0.72 | 60.97 ± 6.44 | 75.29 ± 17.14 |
| Phosphatidylcholine | 92.49 ± 2.56 | 41.47 ± 12.96 | 73.67 ± 4.12 |
| Ribavirin | 68.67 ± 10.70 | 89.05 ± 6.04 | 90.14 ± 0.83 |

Figure 3:
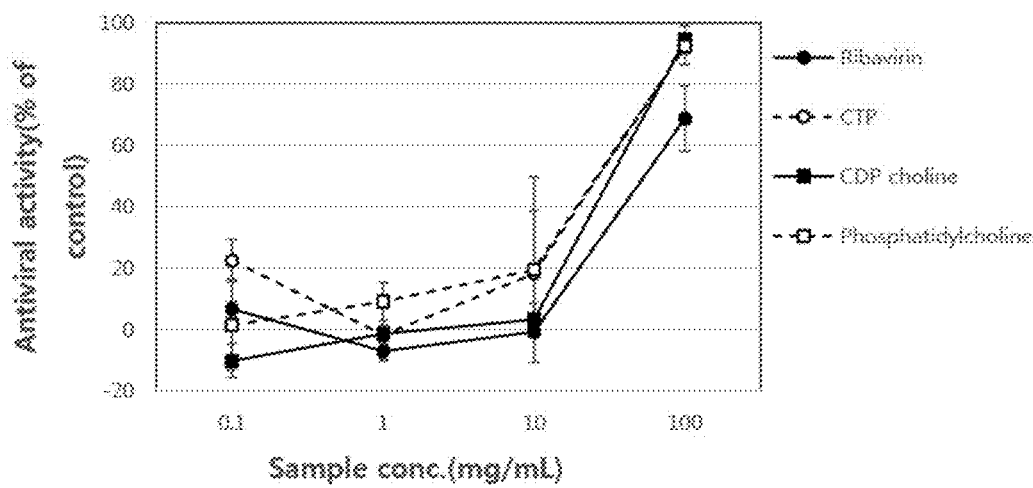
FIG. 3 shows an effect of inhibiting proliferation of *rhinovirus* type 2 according to the concentration of substances involved in the phosphatidylcholine synthesis pathway.
Figure 4:
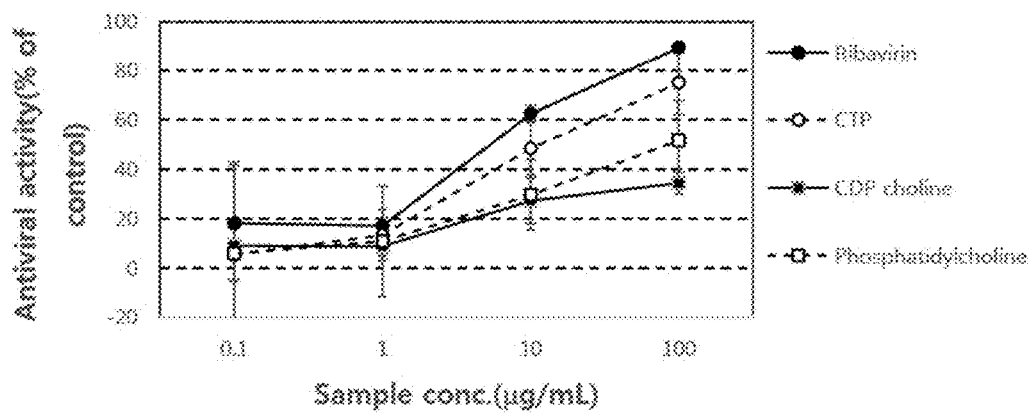
FIG. 4 shows an effect of inhibiting proliferation of *rhinovirus* type 3 according to the concentration of substances involved in the phosphatidylcholine synthesis pathway.
Figure 5:
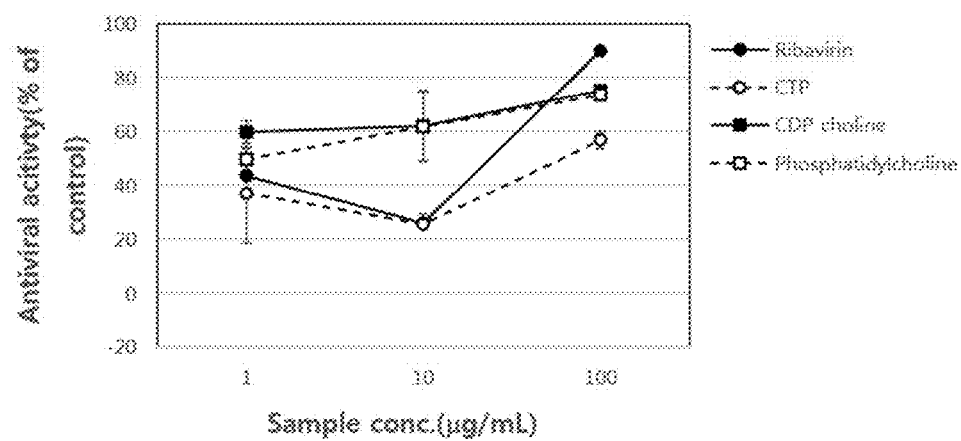
FIG. 5 shows an effect of inhibiting proliferation of *rhinovirus* type 5 according to the concentration of substances involved in the phosphatidylcholine synthesis pathway.

The antiviral abilities (%) against *rhinovirus* type 2, type 3, and type 5 according to the drug concentration are shown in FIGS. 3 to 5, respectively.

As shown in FIG. 3, the anti-*rhinovirus* activity of cytidine triphosphate, CDP-choline, and phosphatidylcholine of the present invention was increased as the concentration thereof increased. Therefore, it was confirmed that cytidine triphosphate, CDP-choline, and phosphatidylcholine of the present invention have a superior effect of inhibiting proliferation of *rhinovirus* type 2 at the concentration of 1µg/ml or more, compared to that of ribavirin, an antiviral agent used as the control group.

Further, as shown in Table 4, the anti-*rhinovirus* activity of cytidine triphosphate and CDP-choline of the present invention was increased as the concentration thereof increased. It was confirmed that cytidine triphosphate, CDP-choline, and phosphatidylcholine have a similar or superior effect of inhibiting *rhinovirus* type 3 even at the low concentration of 0.1 µg/ml, compared to that of ribavirin, an antiviral agent used as the control group.

Furthermore, as shown in Table 5, cytidine triphosphate, CDP-choline, and phosphatidylcholine similarly inhibited *rhinovirus* type 5 at the concentration of 100 µg/ml compared to ribavirin which was used as the control group. Therefore, it was confirmed that cytidine triphosphate, CDP-choline, and phosphatidylcholine have the anti-*rhinovirus* activity.

EXAMPLE 2

Antiviral Activity Test Against *Enterovirus*

Figure 6:
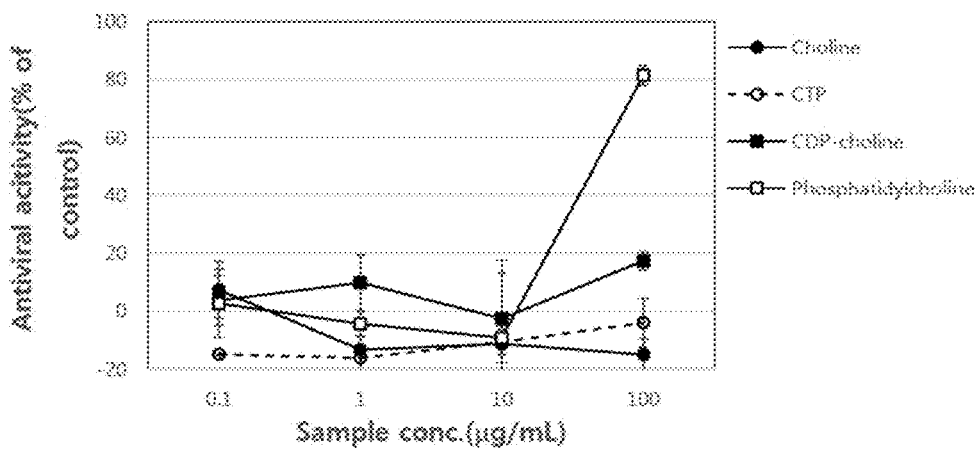
FIG. 6 shows an effect of inhibiting proliferation of *coxsackievirus* type A according to the concentration of substances involved in the phosphatidylcholine synthesis pathway.

Vero cells ($2\times10^4$ cells) were placed in each well of 96-well plates and cultured for 24 hours. After 24 hours, the culture supernatant of each well was removed, and then coxsackievirus type A solution or type B solution, which is a type of *enterovirus*, titrated with TCID50 was placed in each well. In addition, as shown in FIG. 6, choline, cytidine triphosphate, CDP-choline, and phosphatidylcholine were added thereto at concentrations of 0.1 µg/ml, 1µg/ml, 10 µg/ml, and 100 µg/ml. As a result, it was confirmed that the antiviral activity of cytidine triphosphate, CDP-choline, and phosphatidylcholine increased as the concentration thereof increased. Further, it was also confirmed that the antiviral activity of phosphatidylcholine was significantly remarkable at the concentration of 100 µg/ml compared to that of ribavirin, an antiviral agent used as the control group (Table 2).

TABLE 2

| Classification | Drug concentration (100 μg/mL) | |
| --- | --- | --- |
| | Coxsackievirus type A | Coxsackievirus type B |
| Cytidine triphosphate | −4.06 ± 8.41 | 32.55 ± 1.24 |
| CDP-choline | 17.23 ± 3.05 | 26.75 ± 6.97 |
| Phosphatidylcholine | 81.45 ± 3.44 | 26.18 ± 1.69 |
| Ribavirin | 31.07 ± 3.72 | 19.57 ± 4.30 |

Figure 7:
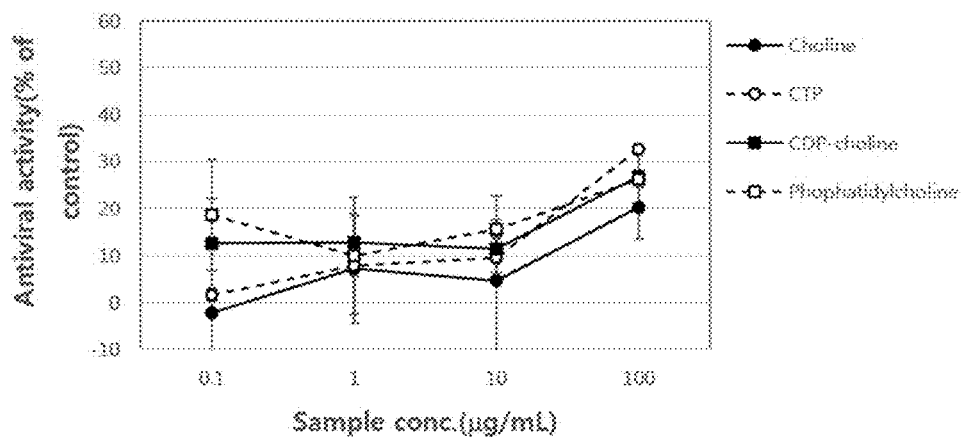
FIG. 7 shows an effect of inhibiting proliferation of *coxsackievirus* type B according to the concentration of substances involved in the phosphatidylcholine synthesis pathway.

The antiviral abilities (%) against coxsackievirus type A and type B according to the drug concentration are shown in FIGS. 6 and 7, respectively.

As shown in FIG. 7, it was confirmed that the antiviral activity of cytidine triphosphate and CDP-choline of the present invention against coxsackievirus type B increased as the concentration thereof increased. Further, it was also confirmed that cytidine triphosphate, CDP-choline, and phosphatidylcholine exhibited a higher antiviral effect at the concentration of 100 μg/ml compared to ribavirin which was used as the control group.

EXAMPLE 3

Inhibitory Activity of Viral RNA Production

In order to confirm mechanism of the composition of the present invention, which inhibits the necrosis of virus-infected cells, the following experiment was conducted.

Figure 8:
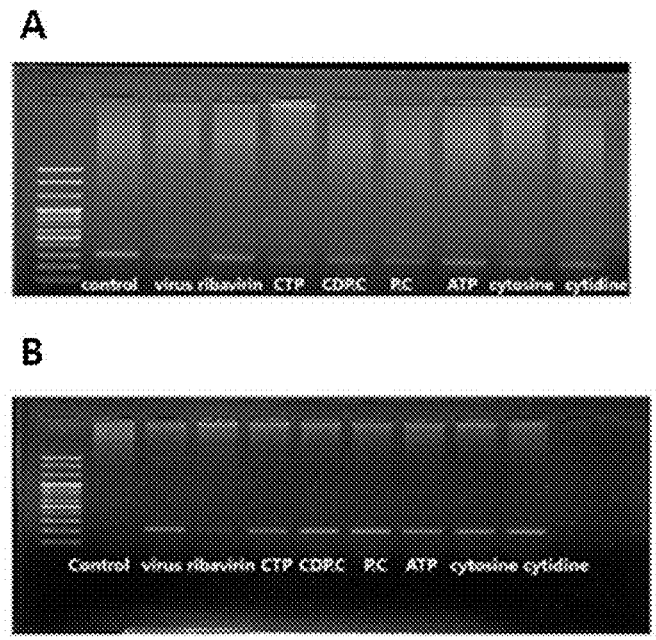
FIG. 8 shows a result that substances involved in the phosphatidylcholine synthesis pathway are not involved in inhibition of *rhinovirus* RNA synthesis.

In FIG. 8-A, HeLa cells were cultured in a 6-well plate, followed by infecting *rhinovirus* type 2 with TCID50. Thereafter, ribavirin, CDP-choline, phosphatidylcholine, ATP, and CTP were added to each well, and then RNA was respectively isolated from the cells in each well after 48 hours. cDNA was prepared using reverse transcriptase from the same amount of the extracted RNA, and beta-actin genes (300 bp) were amplified using a beta-actin-specific primer set. The result thereof is represented in FIG. 8-A, and it was confirmed that beta-actin genes in all wells were amplified in similar amounts.

In FIG. 8-B, *rhinovirus* genes (188 bp) were amplified using a *rhinovirus*-specific primer from cDNA previously prepared. The result thereof is represented in FIG. 8-B. The result showed that the amount of RNA in virus was reduced by administering ribavirin, of which the effect of inhibiting nucleic acid proliferation of RNA virus is known. However, the amount of RNA in virus was not reduced when CDP-choline, phosphatidylcholine, ATP, and CTP were administered. As a result, it was confirmed that CDP-choline, phosphatidylcholine, ATP, and CTP did not affect the production of RNA in virus.

EXAMPLE 4

Activity of Inhibiting Necrocytosis in Virus-infected Cells

Figure 9:
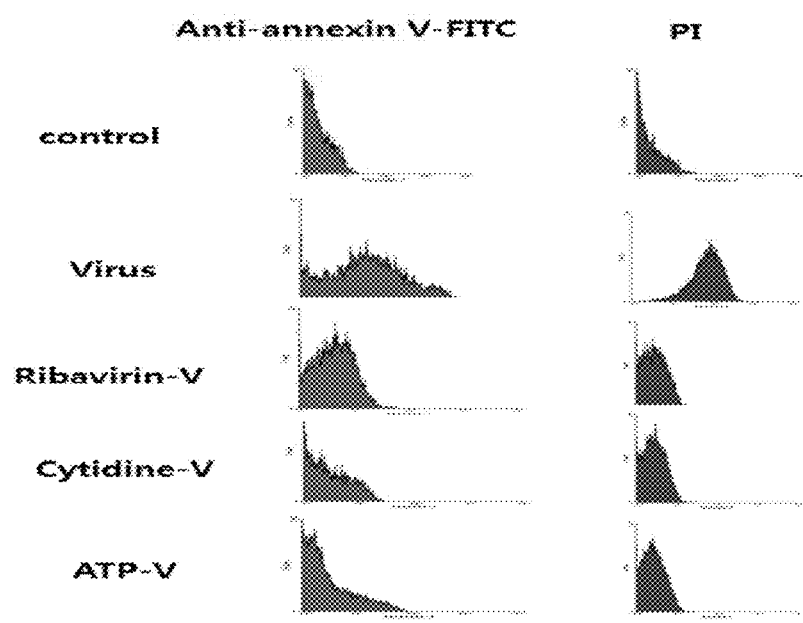
FIG. 9 shows an effect in which substances involved in the phosphatidylcholine synthesis pathway inhibit necrocytosis caused by *rhinovirus* infection.

It was observed that an antibody response against Annexin, a marker protein for necrocytosis, increased in virus-infected cells. However, the antibody response against Annexin also did not appear in the cell group to which cytidine, a precursor of CTP, which is an inducer of CDP-choline synthesis, was administered, as with the ribavirin-administered group. It is predicted that cytidine inhibits necrocytosis as cytidine participates, along with ATP, in the phosphatidylcholine synthesis pathway, which is a process of converting intracellular choline into phosphatidylcholine, while cytidine is converted into cytidine triphosphate by intracellular cytidine triphosphate synthase (FIG. 9).

Based on the results above, it was confirmed that substances involved in the phosphatidylcholine synthesis pathway inhibited the necrosis of virus-infected cells by mechanisms different from ribavirin.

PREPARATION EXAMPLE 1

Preparation of Pharmaceutical Formulations

The following antiviral composition comprises at least one selected from the group consisting of choline, phosphocholine, cytidine triphosphate, CDP-choline, phosphorylcholine, and phosphatidylcholine.

1-1 Preparation of Powders

| | |
| --- | --- |
| Antiviral composition of the present invention | 2 g |
| Lactose | 1 g |

The ingredients were mixed and filled into sealed packaging to provide powders.

1-2 Preparation of a Tablet

| | |
| --- | --- |
| Antiviral composition of the present invention | 100 mg |
| Cornstarch | 100 mg |
| Lactose | 100 mg |
| Magnesium stearate | 2 mg |

The ingredients were mixed and tabletted according to a conventional tablet preparation method to prepare a tablet.

1-3 Preparation of a Capsule

| | |
| --- | --- |
| Antiviral composition of the present invention | 100 mg |
| Cornstarch | 100 mg |
| Lactose | 100 mg |
| Magnesium stearate | 2 mg |

The ingredients were mixed and filled into a gelatin capsule according to a conventional capsule preparation method to prepare a capsule.

1-4 Preparation of a Pill

| | |
| --- | --- |
| Antiviral composition of the present invention | 1 g |
| Lactose | 1.5 g |
| Glycerin | 1 g |
| Xylitol | 0.5 g |

The ingredients were mixed and prepared into a pill according to a conventional method in such a manner that one pill has a weight of 4 g.

1-5 Preparation of a Granule

| | |
| --- | --- |
| Antiviral composition of the present invention | 150 mg |
| Soybean extract | 50 mg |
| Glucose | 200 mg |
| Starch | 600 mg |

The ingredients were mixed and 100 mg of 30% ethanol was added thereto, followed by drying at 60° C. After formation of granules, the granules were filled into packaging.

PREPARATION EXAMPLE 2

Preparation of a Feed 2-1 Preparation of a Feed Additive

| Antiviral composition of the present invention | 0.1% to 10% |
|---|---|
| Tricalcium phosphate | 1% to 20% |
| Vitamin E | 0.01% to 0.1% |
| Enzyme powders | 1% to 10% |
| Lactic acid bacteria | 0.1% to 10% |
| Glucose | 20% to 90% |

2-2 Preparation of a Feed

A feed was prepared with the feed additive of Preparation Example 2-1 as an active ingredient, and the following ingredients are comprised therein.

| Feed additive of Preparation Example 2-1 | 0.1% to 10% |
|---|---|
| Wheat bran | 40% to 49.9% |
| Milo | 21.20% |
| Soybean meal | 20.00% |
| Fish meal | 3.00% |
| Molasses | 4.00% |
| Mineral | 1.53% |
| Vitamin | 0.27% |

Accordingly, since the composition for inhibiting viral proliferation according to the present invention is harmless to the human body and exhibits an excellent effect for inhibiting the viral proliferation, it can be applied to a pharmaceutical composition for preventing or treating viral diseases, and to a health functional food, a quasi-drug composition, and a feed composition for preventing or ameliorating viral diseases.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

INDUSTRIAL APPLICABILITY

The composition for inhibiting viral proliferation according to the present invention can be applied to a pharmaceutical composition for preventing or treating viral diseases, and to a health functional food, a quasi-drug composition, and a feed composition for preventing or ameliorating viral diseases.

The invention claimed is:

1. A method of enhancing antiviral activity in a subject infected by a virus, comprising administering an antiviral composition to the subject, wherein the virus belongs to the family picornaviridae and the composition comprises at least one substance involved in phosphatidyl synthesis pathway, selected from the following group:
   i) choline;
   ii) phosphocholine;
   iii) cytidine diphosphate-choline (CDP-choline);
   iv) phosphorylcholine; and
   v) phosphatidylcholine.

2. The method of claim 1, wherein the composition further comprises cytidine triphosphate (CTP).

3. The method of claim 1, wherein the virus is any one selected from the group consisting of *rhinovirus, enterovirus, cardiovirus, aphthovirus*, and *hepatovirus*.

4. The method of claim 3, wherein the *rhinovirus* is any one selected from the group consisting of *rhinovirus* type 2, type 3, and type 5.

5. The method of claim 3, wherein the *enterovirus* is *coxsackievirus* type A or *coxsackievirus* type B.

6. A method for treating a subject infected by a viral disease, comprising administrating an antiviral composition to the subject, wherein the virus belongs to the family picornaviridae and the composition comprises at least one substance involved in phosphatidyl synthesis pathway, selected from the following group:
   i) choline;
   ii) phosphocholine;
   iii) cytidine diphosphate-choline (CDP-choline);
   iv) phosphorylcholine; and
   v) phosphatidylcholine.

7. The method of claim 6 for treating a viral disease, wherein the viral disease comprises any one selected from the group consisting of cold, enteritis, hand-foot-mouth disease, viral meningitis, pneumonia, encephalitis, neurogenic pulmonary edema, conjunctivitis, encephalomyocarditis, myocarditis, hepatitis, poliomyelitis, paralysis, vesicular disease, myositis, pancreatitis, epidemic myalgia, herpangina, asthma, chronic obstructive pulmonary disease, sinusitis, and tympanitis.

8. The method of claim 6 for treating a viral disease, wherein the viral disease is a cold.

9. The method of claim 6, wherein the composition further comprises cytidine triphosphate (CTP).

10. A method of enhancing antiviral activity in a subject, comprising administering an antiviral composition to the subject infected by a virus, wherein the virus is any one selected from the group consisting of rhinovirus type 2, rhinovirus type 3, rhinovirus type 5, *coxsackievirus* type A and *coxsackievirus* type B, and the composition comprises cytidine triphosphate (CTP).

* * * * *